USO05558937A

United States Patent [19]
Woods et al.

[11] Patent Number: 5,558,937
[45] Date of Patent: Sep. 24, 1996

[54] OPTICAL FIBER PRIMARY COATINGS AND FIBERS COATED THEREWITH

[75] Inventors: John G. Woods, Farmington, Conn.; Margaret A. Rakas, Longmeadow, Mass.; Anthony F. Jacobine, Meriden; Louis M. Alberino, Chesire, Conn.; Philip L. Kropp, Newington, Conn.; Donna M. Sutkaitis, Cheshire, Conn.; David M. Glaser, New Britain, Conn.; Steven T. Nakos, Andover, Conn.

[73] Assignee: Loctite Corporation, Hartford, Conn.

[21] Appl. No.: 433,722

[22] Filed: May 3, 1995

Related U.S. Application Data

[60] Division of Ser. No. 80,748, Jun. 22, 1993, Pat. No. 5,459,175, which is a continuation-in-part of Ser. No. 619,068, Nov. 28, 1990, and a continuation-in-part of Ser. No. 56,128, Apr. 30, 1993, Pat. No. 5,399,624, which is a continuation-in-part of Ser. No. 746,649, Aug. 16, 1991, Pat. No. 5,208,281, which is a continuation-in-part of Ser. No. 651,271, Feb. 5, 1991, Pat. No. 5,167,882, which is a continuation-in-part of Ser. No. 632,391, Dec. 21, 1990, abandoned.

[51] Int. Cl.$^6$ .............................. G02B 6/00; D02G 3/00; C08G 75/12; C08F 2/50
[52] U.S. Cl. ..................... 428/378; 385/145; 522/180; 522/181; 528/307; 528/376
[58] Field of Search ........................... 522/180, 181; 528/376, 307; 385/145; 428/378

[56] References Cited

U.S. PATENT DOCUMENTS

| | | | |
|---|---|---|---|
| 4,125,644 | 11/1978 | Ketley et al. | 427/36 |
| 4,474,830 | 10/1984 | Taylor | 427/54.1 |
| 4,765,712 | 8/1988 | Bohannon, Jr. et al. | 350/96.23 |
| 4,808,638 | 2/1989 | Steinkraus et al. | 522/180 |
| 4,913,859 | 4/1990 | Overton et al. | 264/1.4 |
| 4,935,455 | 6/1990 | Huy et al. | 522/99 |
| 4,946,874 | 8/1990 | Lee et al. | 522/14 |
| 4,956,198 | 9/1990 | Shama et al. | 427/54.1 |
| 4,962,992 | 10/1990 | Chapin et al. | 350/96.23 |
| 4,973,611 | 11/1990 | Puder | 522/42 |
| 5,026,409 | 6/1991 | Robinson et al. | 65/3.11 |
| 5,028,661 | 7/1991 | Clark et al. | 525/189 |
| 5,034,490 | 7/1991 | Jacobine et al. | 528/30 |
| 5,167,882 | 12/1992 | Jacobine et al. | 264/22 |
| 5,171,816 | 12/1992 | Jacobine et al. | 528/15 |
| 5,182,360 | 1/1993 | Jacobine et al. | 528/205 |
| 5,208,281 | 5/1993 | Glaser | 524/189 |

FOREIGN PATENT DOCUMENTS

0428342A2  5/1991  European Pat. Off. .

OTHER PUBLICATIONS

Product Data Sheet: "QO® POLYMEG® Polyols, General Information, Handling and Properties", QO Chemicals, Inc., 1990.

(List continued on next page.)

*Primary Examiner*—Susan W. Berman
*Attorney, Agent, or Firm*—Vidas, Arrett, & Steinkraus, P.A.

[57] ABSTRACT

A curable thiol-ene composition specially adapted for use as a primary coating on optical fibers comprises a polythiol and a compound having a plurality of norbornene groups thereon, are characterized in that one of either the compound having the plurality of norbornene groups or the polythiol has a backbone of a poly(tetramethylene oxide), or is an oligomer thereof, and the poly(tetramethylene oxide) has a molecular weight of between 250 and 5,000. The formulations are relatively low viscosity liquids at practical application temperatures and cure substantially completely with very low irradiation fluence. The formulations cure in ambient air. There is no need to exclude oxygen or to control humidity. The formulations of the invention can be cured using low intensity UV lamps which do not generate significant amounts of heat. The cured products have excellent low temperature flexibility, good humidity and water absorbtion resistance and good thermal oxidative stability. The formulations may be applied to optical fibers using conventional techniques and cured with UV-vis or EB irradiation.

20 Claims, 1 Drawing Sheet

OTHER PUBLICATIONS

"A New Derivation of Average Molecular Weights of Nonlinear Polymers", C. W. Macoski & D. R. Miller, Molecular Weights of Nonlinear Polymers, vol. 9, No. 2, Mar.–Apr. 1976.

"Thermo–Oxidative Aging of a Primary Lightguide Coating in Films and Dual–Coating in Films and Dual–Coated Fibers", D. A. Simoff, M. G. Chan, J. T. Chapin & B. J. Overton, Polymer Engineering and Science, Mid–Sep. 1989, Vol. 29, No. 17.

"A Dynamic Modal for Optical–Fiber Coating Application", D. H. Smithgall, Journal of Lightware Technology vol. 8, No. 10, Oct. 1990.

"Fiber Optics:New Eyes of Industry", J. Holusha, The New York Times, Nov. 6, 1991.

"Time–Temperatue Dependence of Dual Coated Lightguide Pullout Measurements", B. J. Overton & C. R. Taylor, Polymer Engineering and Science, Mid–Sep. 1989, vol. 29, No. 17.

Jacobine et al, "Photocrosslinked Norbornene–Thiol Copolymers: Synthesis, Mechanical Properties, and Cure Studies", Journal of Appl. Sci. vol. 45, 471–485, 1992.

OPTICAL FIBER PRIMARY COATINGS AND FIBERS COATED THEREWITH

CROSS-REFERENCE TO RELATED APPLICATIONS

This application is a division of application Ser. No. 08/080,748, filed Jun. 22, 1993, now U.S. Pat. No. 5,459,175, which is a continuation-in-part of copending application, Ser. No. 07/619,068, filed Nov. 28, 1990 pending and a continuation-in-part of Ser. No. 08/056,128, filed Apr. 30, 1993, now U.S. Pat. No. 5,399,624, incorporated herein by reference, which is a continuation-in-part of Ser. No. 07/746,649, filed Aug. 16, 1991, U.S. Pat. No. 5,208,281, incorporated herein by reference, which is a continuation-in-part of Ser. No. 07/651,271, filed Feb. 5, 1991, U.S. Pat. No. 5,167,882, incorporated herein by reference, which is a continuation-in-part of Ser. No. 632,391, filed Dec. 21, 1990, abandoned.

TECHNICAL FIELD

This invention relates to a primary coating material for optical fibers and to optical fibers having primary coatings thereon.

BACKGROUND OF THE INVENTION

U.S. Pat. No. 4,913,859 provides a general description of the manufacture of optical fiber as follows:

"In the manufacturing of optical fiber, a glass preform rod which generally is manufactured in a separate process is suspended vertically and moved into a furnace at a controlled rate. The preform softens in the furnace and optical fiber is drawn freely from the molten end of the preform rod by a capstan located at the base of a draw tower.

"Because the surface of the optical fiber is very susceptible to damage caused by abrasion, it becomes necessary to coat the optical fiber, after it is drawn, but before it comes into contact with any surface. Inasmuch as the application of the coating material must not damage the glass surface, the coating material is applied in a liquid state. Once applied, the coating material must become solidified rapidly before the optical fiber reaches a capstan. This may be accomplished by photocuring, for example.

"Those optical fiber performance properties which are selected most by the coating material are strength and transmission loss. Coating defects which may expose the optical fiber to subsequent damage arise primarily from improper application of the coating material. Defects such as large bubbles or voids, non-concentric coatings with unacceptably thin regions, or intermittent coatings must be avoided. When it is realized that the coating thickness may be as much as the radius of an optical fiber, it becomes apparent that non-concentricity can cause losses in splicing, for example.

"Transmission losses may occur in optical fibers because of a mechanism known as microbending. Optical fibers are readily bent when subjected to mechanical stresses, such as those encountered during placement in a cable or when the cabled fiber is exposed to varying temperature environments or mechanical handling. If the stresses placed on the fiber result in a random bending distortion of the fiber axis with periodic components in the millimeter range, Light propagating in the fiber core may escape therefrom. These losses, termed microbending losses, may be very large. Accordingly, the fiber must be isolated from stresses which cause microbending. The properties of the Fiber coating play a major role in providing this isolation, with coating geometry, modulus and thermal expansion coefficient being the most important factors.

"Two types of coating materials are used to overcome this problem. Single coatings, employing a relatively high shear modulus, e.g. $10^9$ Pa, or an intermediate modulus, e.g. $10^8$ Pa, are used in applications requiring high fiber strengths or in cables which employ buffer tubes where fiber sensitivity to microbending is not a significant problem.

"Dual coated optical fibers increasingly are being used to obtain design flexibility and improved performance. A reduction in the modulus of the coating material reduces microbending sensitivity by relieving stress caused in the fiber. Typically, an inner or primary coating layer that comprises a relatively low modulus material, e.g. $10^5$–$10^7$ Pa, is applied to the optical fiber. The modulus of the primary coating should be effective in promoting long bending periods for the fiber which are outside the microbending range. Such a material reduces microbending losses associated with the cabling, installation or environmental changes during the service life of the optical fiber. In order to meet temperature conditions in expected areas of use, the low modulus coating material must be effective in the range of about –40° to 77° C. An outer or secondary coating layer comprising a relatively high modulus material is applied over the primary layer. The outer coating layer is usually of a higher modulus material to provide abrasion resistance and low friction for the fiber and the primary coating layer. The dual coating serves to cushion the optical fiber by way of the primary layer and to distribute the imposed forces by way of the secondary layers, so as to isolate the optical fiber from bending moments."

"After the coating material or materials have been applied to the moving optical fibers, the coating material or materials are cured, typically by exposure to ultraviolet radiation. In some coating systems, a primary coating material is applied and cured by subjecting it to ultraviolet energy prior to the application of the secondary coating material."

Other references pertaining to coatings for optical fibers include: U.S. Pat. No. 4,125,644; U.S. Pat. No. 4,474,830; U.S. Pat. No. 4,9:35,455; U.S. Pat. No. 4,946,874; U.S. Pat. No. 4,956,198; U.S. Pat. No. 4,973,611; U.S. Pat. No. 5,026,409; U.S. Pat. No. 5,139,872; U.S. Pat. No. 5,169,879; Martin, "Contribution of Dual UV Cured Coatings to Optical Fiber Strength and Durability," *Proceedings, Radcure Europe '87*, pp 4–15-4–24 (May 1987); Chawala, et al, "An Infrared Study of Water Absorbtion of UV Curable Optical Fiber Coatings," *Radtech Report*, 24–28 January/February 1992; Smithgall, "A Dynamic Modal for Optical-Fiber Coating Application," *J. Lightwave Technology*, 8, 1584–1590 (October 1990); Sireoff et al, "Thermo-Oxidative Aging of a Primary Lightguide Coating in Films and Dual-Coated Fibers," *Polymer Engineering and Science*, 29, 1177–1181 (Mid-September 1989); and Overton et al, "Time Temperature Dependence of Dual Coated Lightguide Pullout Measurements," *Polymer Engineering and Science*, 29, 1169–1171 (Mid-September 1989).

In U.S. Pat. No. 5,171,609 there is described a common problem encountered in curing of optical fiber coatings, that being the tendency of heat from high energy UV lamps typically employed to cure the coating material to evaporate some coating from the fiber and to deposit same on the wall of the transparent curing chamber, thereby darkening the chamber and reducing energy available to cure the coating. Various mechanical solutions to this problem have been proposed but all are complicated and cumbersome.

SUMMARY OF THE INVENTION

The invention hereof pertains in one aspect to thiol-ene formulations based on norbornene functional polyenes which are uniquely suited for optical fiber primary coatings. The formulations are easily applied, relatively low viscosity, liquids at practical application temperatures and cure substantially completely with very low irradiation fluence. The formulations cure in ambient air. There is no need to exclude oxygen or to control humidity, as is the case with some prior art compositions. The formulations of the invention can be cured using low intensity UV lamps which do not generate significant amounts of heat and therefore do not require special apparatus to avoid evaporation/condensation transfer of coating material from the fiber to the light source window. The cured products have excellent low temperature flexibility, good humidity and water absorbtion resistance and good thermal oxidative stability. The compositions are characterized by use of a norbornene functional polyene or a polythiol which has a poly(tetramethylene oxide) backbone with a molecular weight in the range of about 250 to about 5000. In preferred compositions the polythiol component and the norbornene functional components are fully miscible, suitably by using an oligomeric form of one or the other of the two components.

Cured polymers prepared from the compositions of the invention; optical fibers coated therewith; and methods of preparing such coated fibers by applying the composition as a liquid and then irradiating the coating with UV-vis or EB radiation comprise further aspects of the invention.

The present application is specifically directed to the optical fibers coated with of the compositions of the present invention and cured at high conversion rates- Such optical fibers are thus characterized as having a primary coating thereon which is the addition product, at 80% or greater conversion, of a polythiol and a polyene, the polyene being a compound having a plurality of norbornene groups thereon, one of the polythiol or the polyene having a backbone of a poly(tetramethylene oxide). The poly(tetramethylene oxide) has a number average molecular weight of between 250 and 5,000. The coating is formed by curing a thiol-ene composition comprising said polyene and said polythiol or an oligomer of said. polythiol and said polyene.

DETAILED DESCRIPTION OF THE INVENTION

One type of known apparatus which may be used to draw and coat an optical fiber is described and illustrated in U.S. Pat. No. 4,913,859, incorporated herein by reference. The coatings are suitably cured by UV-vis or EB (electron beam) irradiation.

Figure 1:
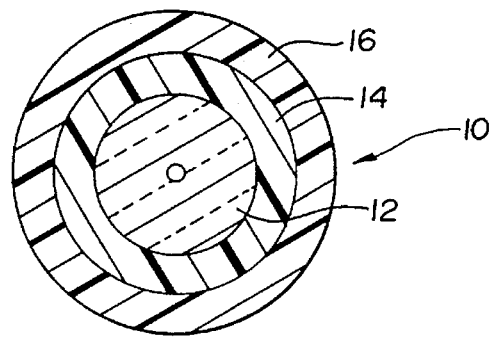
FIG. 1 is an end cross sectional view of an optical fiber which includes primary and secondary protective coating layers.

As mentioned hereinbefore, it is frequently common place to apply dual coatings to a drawn optical fiber. These provide protection for the optical fiber, as well as render the optical fiber more flexible than with a single coating layer. A coated optical fiber 10, comprising optical glass fiber 12, a primary coating 14 adjacent the optical glass fiber and a secondary coating layer 16 overlying the primary coating, is shown in FIG. 1. The present invention pertains to formulations for the primary coating.

The primary coating formulations of the invention are a species of thiol-ene composition, comprising a polyene, a polythiol and a photoinitiator.

The polyenes used in the formulations of the invention are suitably dinorbornene terminated poly(tetramethylene oxide) polymers (also known as poly(TMO) or poly THF). In accordance with convention, molecular weight of the polyether backbone is included in the name of the compound, i.e. hydroxyl terminated poly(tetramethylene oxide 650) [pTMO 650] has an average molecular weight, based on hydroxyl number calculation, of approximately 650. These polyether backbones have been found to provide an especially good combination of low Tg, moisture resistance, low composition viscosity and other desired properties while the thiol-norbornene system provides an especially fast cure. Polyether backbones having molecular weights in the range of 250 to as high as 5000 are suitable, depending on coating application temperature, with molecular weights in the range of 650–2000 being preferred. Most preferably, the molecular weight of the backbone is in the range of 650–1000, as higher molecular weight materials give formulations which are waxy solids at ambient temperature and must be mildly heated in order to be applied.

The norbornene termination of the polyether backbone can be obtained in a variety of ways. Conveniently, hydroxy terminated poly(tetramethylene oxide) can be reacted with hydroxy reactive norbornene functional compounds such as acid chlorides, isocyanates, azlactones and chloroformates. The choice of linkage does influence the properties obtained but generally not so much as the backbone polyether. Examples of suitable-polyethers include the following:

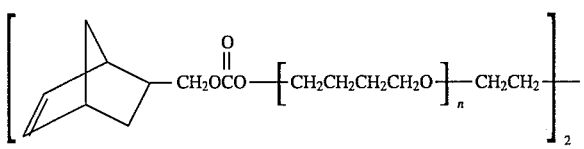

Poly(tetramethylene oxide) di-[(norborn-5-ene-2-)methylcarbonate],

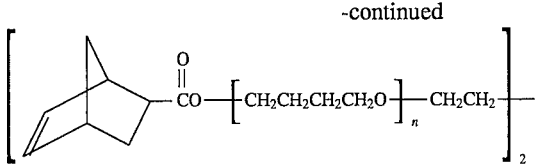

Poly(tetramethylene oxide) di-(norborn-2-ene-5-carboxylate),

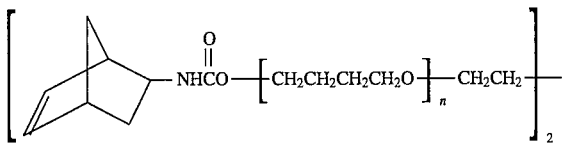

Poly(tetramethylene oxide) di-(norborn-2-ene-5-carbamate) and

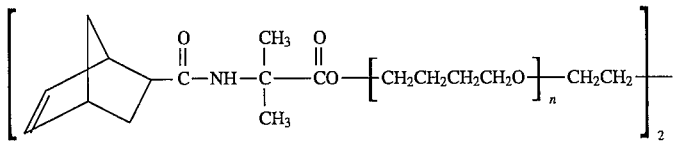

Poly(tetramethylene oxide) di-[2-(norborn-2-ene-5-carboxamido)-2,2-dimethylactate].

Suitably, n is an integer of 1–30.

The polythiol component of the inventive compositions may be derived from any compound having an average of more than two thiol groups per molecule. Comparability with the norbornene functional polyether, however, is important in order to maintain shelf stability of the formulation. Generally trithiol functional compounds, such as trimethylolethane tris-mercaptopropionate, trimethylolpropane tris-mercaptopropionate ([TMP]2), trimethylolethane trismercaptoacetate, and trimethylolpropane tris-mercaptoacetate, will be fully miscible with the norbornene compound and can be used as is.

It has been found that polythiols obtained by esterification of a tetra or higher functionality polyol with an α or β-mercaptocarboxylic acid such as thioglycolic acid, or β-mercaptopropionic acid, especially pentaerythritol tetramercaptoacetate and pentaerythritol tetrakis-β-mercaptopropionate (PETMP) do not always give fully miscible formulations with the result that they sediment on standing and must be throughly remixed to disperse prior to use. This is not desireable for many commercial applications, including high volume optical fiber primary coating applications.

Formulations derived from tetra and higher polythiols, however can be easily employed without the need for remixing at the time of use if the tetra or higher functional polythiol compound is first reacted with a stoichiometric deficiency of a poly(tetramethylene oxide) dinorbornene compound to provide a polythiol terminated oligomer which is then blended with an additional amount of a poly(tetramethylene oxide) dinorbornene compound (which may be the same or different as the compound used to make the polythiol prepolymer) to form the thiolene composition. Suitably, the thiol functionalized poly(TMO) dinorbornene oligomer may be prepared by pre-reacting 1.0 equivalent of PETMP with about 0.3 equivalents of the poly(TMO) dinorbornene monomer. The oligomer is obtained as a solution in PETMP. The new thiol oligomer solution is miscible with the poly(TMO) dinorbornene monomer at equivalent concentrations. Although the viscosity of the modified formulation is higher than the corresponding unmodified blend, the new compositions are clear and homogeneous. The new oligomer assists the solubility of PETMP in the poly(TMO)-norbornene monomer. Sedimentation is not observed on dark storage at ambient temperature over a 24 hour period.

The method used to produce the new monomer is straightforward, fast and requires no additional materials nor special lab equipment. The procedure used is illustrated below in Example 12.

Alternative formulations within the scope of the invention employ a dithiol having a poly(tetramethylene oxide) backbone and a plural norbornene compound having three or more norbornene groups per molecule. For instance, formulations based on pentaerythritol tetrakis-(norbornene carboxylate), or trimethylpropane tri-(norbornene carboxylate), and poly(tetramethylene oxide)(1000) dimercaptopropionate, will give cured properties similar to the di-poly(TMO)norbornene carboxylate/PETMP or [TMP]2 formulations exemplified herein.

The ratio of the polyene to the polythiol component can be varied within a range of ene to thiol groups of from about 1.0:0.8 to about 1.0:1.3. Thiol content below about 1.0:0.8, ene/thiol, in the formulation may not give a composition cureable with the desired low energy input. Thiol content above a ratio of 1.0:1.3, ene/thiol, possibly as high as 1.0:1.5 may be satisfactory in some instances. Generally it is preferred that the ratio of ene to thiol groups be 1:1.

While a curable composition using norbornene functional compounds of the invention may include both difunctional norbornenyl compounds and difunctional thiol compounds, it will be understood that at least a portion of at least one of these components should contain more than two functional groups per molecule to produce a crosslinked product when cured. That is, the total of the average number of norbornene groups per molecule of norbornene functional compound and the average number of coreactive thiol groups per molecule of the thiol functional compound should be greater than 4 when a crosslinked cured product is desired. This total is referred to as the "total reactive functionality" of the composition.

Compositions formulated for electron beam (EB) curing do not require a cure initiator. Compositions formulated for UV-vis or thermal cure will desireably include a photoinitiator or thermal initiator, respectively. The initiator may be radical or cationic. Most suitably it is a free radical photoinitiator. Examples of free radical photoinitiators include benzoin and substituted benzoin compounds, benzophenone, Michler's ketone, dialkoxybenzophenones, dialkoxyacetophenones, peroxyesters described in U.S. Pat. Nos. 4,616,826 and 4,604,295, etc. The photoinitiator is employed in an amount effective for initiating cure of the formulation, typically 0.5–5%. Combinations of two or more photoinitiators may also be employed, for instance to optimize response for a particular UV-vis energy source.

The formulations also preferably include a stabilizer. Preferred stabilizers, described in EP 428,342 incorporated herein by reference, are non-acidic nitroso compounds, particularly N-nitrosohydroxylarylamines and salts thereof. A suitable such compound is the aluminum salt of N-nitrosophenylhydroxylamine (Q1301™, Wako Pure Chemical Industries, Richmond, VA) which may be usefully employed at levels between about 10 ppm and 1%, preferably 100–10,000 ppm.

The thiol-ene formulations which employ norbornene functional polyenes, even with stabilization, are quite sensitive to fluorescent light and may need to be kept in the dark to remain stable for more than a few days. If storage for periods of more than a few months is necessary, separating norbornene and thiol compounds in a two-part formulation may be desireable.

As described in U.S. Pat. No. 5,399,624, purification of the norbornene resin by contacting it with an amphoteric treating agent selected from the group consisting of silicated magnesium oxide, basic aluminum oxide, silica gel, magnesium oxide, magnesium hydroxide, calcium oxide, calcium hydroxide, barium oxide, and barium hydroxide, and then separating the resin from the treating agent prior to mixture with the polythiol significantly improves the shelf life of the thiol-ene formulation formed therefrom. As described in U.S. Pat. No. 5,371,181, incorporated herein by reference, similar treatment of the polythiol component may also be desirable to stabilize the cure speed performance of the composition on aging and to further stabilize the shelf-life of the formulation.

As described in U.S. Pat. No. 5,208,281, triiodide and other polyiodides have also been found useful shelf-life stabilizers for thiol-ene formulations based on norbornene resins. Suitable polyiodide stabilizers may be $KI/I_2$ (1:2 parts by wt) solutions in water at levels providing 10–2,000 ppm $I_2$, preferably 30–800 ppm $I_2$. An aqueous $KI/I_2$ solution in which the concentration of $I_2$ is 1N is a suitable such solution. Compatible organic solvents such as lower alcohols may also be employed to introduce a polyiodide stabilizer into the formulation. The $KI/I_2$ solution is suitably added to either the norbornene resin or the thiol resin prior to mixing.

Alternatively, as described in U.S. Pat. No. 5,459,173, the formulation may be stabilized with a stabilizer system comprising an alkenyl substituted phenolic compound and one or more compounds selected from the group consisting of a free radical scavenger, a hindered phenolic antioxidant and a hydroxylamine derivative. Examples of suitable alkenyl substituted phenolic compounds include 2-propenylphenol, 4-acetoxy styrene, 2-allylphenol, isoeugenol, 2-ethoxy-5-propenylphenol, 2-allyl-4-methyl-6-t-butylphenol, 2-propenyl-4-methyl-6-t-butylphenol, 2-allyl-4,6-di-t-butylphenol, 2-propenyl- 4,6-di-t-butylphenol and 2,2'-diallyl-bisphenol A, suitably at levels of 500 ppm–5000 ppm by weight of the composition. Preferably the alkenyl phenolic compound is used with a N-nitrosoarylhydroxylamine salt, a radical scavenger such as p-methoxy phenol (MEHQ), and a hindered phenolic antioxidant such as butylated hydroxy toluene (BHT).

The formulations of the invention are characterized by very low viscosities for low Tg organic polymer forming compositions. Formulations employing poly(tetramethylene oxide) backbones of 1000 MW or less are liquids at ambient temperature with typical 25° C. viscosities of 2000 mPas or less. Using trithiols, clear homeogeneous liquid formulations can be readily prepared having viscosities below 1000 mPas or less.

Glass transition temperatures of the cured polymers are very low, no more than −10° C., typically less than −20° C. and in the preferred formulations less than −35° C. Cured polymers whose Tg is below −50° C. can be readily produced, as illustrated in examples 14 and 18–21.

To strengthen adhesion in the interface between the glass fiber and the coating material it is recommended that an adhesion promoter also be employed in the formulation. Suitable adhesion promoters which may be employed are identified in U.S. Pat. No. 5,028,661, incorporated herein by reference, and various other organic acid and silane compounds known to be useful for promoting adhesion, especially to glass. Examples of adhesion promoters include acrylic and norbornene acid phosphate esters; itaconic, acrylic and methacrylic acids; maleic, fumaric and norbornene dicarboxylic acids and their half esters; and, especially, thiol, epoxy, norbornene, acrylic or methacrylic functional silane compounds having two or three hydrolyzable groups bound to silicon. Examples of such silane compounds include 3-methacryloxypropyl trimethoxysilane, mercaptopropyl trimethoxysilane, glycidoxypropyl trimethoxysilane, and the like. The adhesion promoters are employed at conventional levels, suitably about 0.1–3.0 percent by weight of the formulation.

The invention may be illustrated by the following non-limiting examples.

EXAMPLE 1

Synthesis of endo, exo-Norborn-2-ene-5-carbonyl Chloride, I

In a 1000 ml four-necked, round-bottomed flask that was equipped with a magnetic stirrer, an efficient condenser, a constant pressure addition funnel, and a thermometer that was connected to a Thermowatch™ thermostatic controller was stirred acryloyl chloride (271.8 g, 3.00 mol) under a nitrogen atmosphere. Freshly cracked and distilled cyclopentadiene monomer (198.2 g, 3.00 mol) was added at such a rate that the reaction temperature did not exceed 80°–90° C. at any time during the addition. When the addition was completed the reaction was stirred for an additional three hours. Residual starting materials were removed using a water aspirator and the crude reaction mixture was then distilled in vacuo to give the purified product (b.p. 66°–70° C. at 4 mm Hg).

EXAMPLE 2

Synthesis of endo, exo-Norborn-2-ene-5-methyl-5-carbonyl Chloride, II

In a 1000 ml four-necked, round-bottomed flask that was equipped with a magnetic stirrer, an efficient condenser, a constant pressure addition funnel, and a thermometer that was connected to a Thermowatch™ thermostatic controller was stirred freshly distilled methacryloyl chloride (250 g, 2.391 mol, Aldrich Chemical Co.) under a nitrogen atmosphere. Freshly cracked and distilled cyclopentadiene monomer (172;.62. g, 2.63 mol) was added at such a rate that the reaction temperature did not exceed 80°–90° C. at any time during the addition. When the addition was completed the reaction was stirred for an additional three hours. Residual starting materials were removed using a water aspirator and the crude reaction mixture was then distilled in vacuo to give the purified product (b.p. 74°–76° C. at 4–7 mm Hg).

EXAMPLE 3

Synthesis of endo, exo-Norborn-2-ene-5-isocyanate, III

Sodium azide (228.47 g, 3.51 mol in 250 ml deionized water) was added dropwise to a stirred solution of norborn-2-ene-5-carbonyl chloride (500 g., 3.19 mol) and tetra-(n-butyl)ammonium bromide (2.5 g, 0.0077 mol) in dichloromethane (1000 ml) in a 4 liter beaker which had been cooled to 5°–10° C. and maintained at this temperature throughout the reaction. After the addition was completed, the organic layer was separated and dried over anhydrous sodium sulfate and filtered. The filtered solution was then added dropwise to a 2 L round-bottomed flask that was set up for distillation containing benzene (500 ml) maintained at 70° C. Dichloromethane was removed by distillation (overhead temperature 50°–55° C.) and collected. After the addition was completed the temperature of the reaction mixture was maintained at 70° C. for two hours, The reaction mixture was then concentrat on a rotary evaporator and distilled in vacuo. The purified product was collected as a fraction b.p. 6°–65° C. at 115 mm Hg.

EXAMPLE 4

Synthesis of endo, exo-2-(Norborn-5-ene-5)-4,4-dimethyloxazoline-5-one Norbornene Azlactone (NAz), IV In a 1000 ml four-necked, round-bottomed flask that was equipped with a magnetic stirrer, an efficient condenser, a constant pressure addition funnel, and a thermometer was stirred 2-vinyl-4,4-dimethyloxazoline-5-one (501.66 g, 3.61 mol, SNPE, Inc., Princeton, N.J.) under a nitrogen atmosphere. The solution was thermostated at 40° C. by means of a Thermowatch™ Controller and freshly cracked and distilled cyclopentadiene monomer (262.3 g, 3.97 mol) was added at such a rate that the reaction temperature did not exceed 9°–100° C. over the course of the addition. When the addition was completed the reaction was aged at 95° C. for two hours and then concentrated on a rotary evaporator to remove excess cyclopentadiene monomer. The crude mixture was distilled in vacuo (b.p. 7°–73° C. at 0.2 mm Hg) to yield the purified product (yield 689.7 g, 93% Th.) as a colorless liquid that rapidly solidified at room temperature. High field NMR analysis (300 MHz) indicated that the distillate was a mixture of endo and exo isomers of the desired product and was essentially pure,

EXAMPLE 5

Synthesis of Norborn-5-ene-2-methyl Chloroformate, V

Norborn-5-ene-2-methanol (196.20 g, 1.58 mol, Aldrich Chemical Co.) was stirred in toluene (250 ml) in a 1000 ml three-necked, round-bottomed flask that was equipped with a magnetic stirrer, a dry ice condenser, a constant pressure addition funnel, and a thermometer. The reaction was carried out under a nitrogen atmosphere and the outlet of the bubble tube was vented into a dilute solution of sodium hydroxide. The solution was cooled to around 10° C. and a solution of phosgene (171.9 g, 1.738 mol) in toluene (250 ml) was added dropwise at such a rate that the reaction temperature did not exceed 25° C. at any time. When the addition was completed the reaction was warmed to room temperature and stirred for sixteen hours. Excess phosgene was removed by a subsurface nitrogen sparge at 30° C. for three hours. Excess solvent was removed on a rotary evaporator and the purified product was obtained by flash vacuum distillation (oil temperature 150° C., b.p. 75°–80° C. at 1.5 mm Hg).

EXAMPLE 6

Synthesis of Poly(tetramethylene oxide 650) Di-(Norborn-5-ene-2-)methyl Carbonate, VI Hydroxy terminated poly(tetramethylene ether 650) (232.91 g, 0.719 eq. OH) and pyridine (64.3 g, 0.814 mol) was stirred in toluene (300 ml) under a nitrogen atmosphere in a 1000 ml four-necked, round-bottomed flask equipped with mechanical stirring, a thermometer and a constant pressure addition funnel containing norborn-5-ene-2-methyl chloroformate (150 g, 0.74 mol). The chloroformate was added dropwise at such a rate that the reaction temperature slowly climbed to 60° C. during the addition. When the addition was completed the reaction mixture was aged at 70° C. for three hours at which point methanol (5.0 g, 0.16 mol) was added to the reaction mixture. The reaction mixture was filtered through Celite™ diatomaceous earth and the filtrate was concentrated on a rotary evaporator to remove solvent. The crude yellow oil was then passed through a two inch wiped film evaporator at 125° C. and 0.3 mm Hg. The yield of product was 328 g.

EXAMPLE 7

Synthesis of Poly(tetramethylene oxide 650) Di-(Norborn-2-ene-5-Carboxylate), VII Hydroxy terminated poly(tetramethylene oxide 650, Poly(TMO) (401.94 g, 1.241 eq. OH, BASF Corporation, Parsippany, N.J.) and pyridine (111.06 g, 1.41 mol) was stirred in toluene (400 ml) under a nitrogen atmosphere in a 2000 ml four-necked, round-bottomed flask equipped with mechanical stirring, a thermometer and a constant pressure addition funnel containing norborn-2-ene-5-carbonyl chloride (200 g, 1.278 mol). The acid chloride was added dropwise at such a rate that the reaction temperature slowly climbed to 70° C. during the addition. When the addition was completed the reaction mixture was aged at 70° C. for three hours at which point methanol (5.0 g, 0.16 mol) was added to the reaction mixture. The reaction mixture was filtered through Celite™ diatomaceous earth and the filtrate was concentrated on a rotary evaporator to remove solvent. The crude oil was then passed through a two inch wiped film evaporator at 125° C. and 0.4 mm Hg. The yield of product was 535 g (96.5% Th.).

EXAMPLE 8

Synthesis of Poly(tetramethylene oxide 650) Di-(Norborn-2-ene-5-Carbamate), VIII Hydroxy terminated poly(tetramethylene oxide 650) (174.74 g) was stirred under a nitrogen atmosphere with diazabicycloundecane (0.5 g) in a 500 ml four-necked, round-bottomed flask equipped with mechanical stirring, a thermometer, and a constant pressure addition funnel containing norborn-2-ene-5-isocyanate (75 g, 0.556 mol). The addition of isocyanate was controlled at such a rate that the reaction temperature did not exceed 35° C. during the addition period. The reaction mixture was then heated to 70°

C. and held at that temperature for six hours. When infrared spectroscopic analysis showed no further change in the NCO band, the reaction mixture was cooled and the crude oil was then passed through a two inch wiped film evaporator at 125° C. and 0.4 mm Hg. The yield of crude oil was 243.3 g.

EXAMPLE 9

Synthesis of Poly(tetramethylene oxide 650) Di-[2-(Norborn-2-ene-5 Caboxamido)-2,2-Dimethylacetate], IX A mixture of 2-(Norborn-2-ene-5)-4,4-dimethyloxazolin-5-one (130.36 g, 0.636 mol), hydroxy terminated poly(tetramethylene oxide 650) (200 g) and diazabicycloundecane (3.31 g) was stirred under a nitrogen atmosphere in a 1000 ml four-necked, round-bottomed flask equipped with mechanical stirring, and efficient condenser and a thermometer. The reaction mixture was heated to 100° C. After eight hours infrared spectroscopy indicated that the distinctive azlactone carbonyl band at 1817 $cm^{-1}$ had completely disappeared. The crude product was then passed through a two inch wiped film evaporator at 125° C. and 0.4 mm Hg. The yield of viscous oil was 314.8 g.

EXAMPLE 10

Mechanical Properties or Norbornene-Thiol Copolymers

Curable compositions were prepared by mixing equivalent amounts of norbornene functional resins with PETMP and photoinitiator (DAROCUR® 1173, sold by EM Industries, Hawthorne, N.Y.). Specimens for mechanical testing were cured on a Fusion™ System conveyerized dual lamp system (two D bulbs). Tensile properties were determined on an Instron™ Universal Testing Machine Model 4505 using 20 mil films according to a modified ASTM D-883 test. Dynamic mechanical tests were carried out on a Rheometrics Dynamic Analyzer RDA II with torsion rectangular geometry. Strain sweeps were carried out on duplicate samples to insure that temperature sweeps were carried out in the linear response region. Results of testing several formulations using several norbornene terminated poly(tetramethylene oxide) polyenes are shown in Table 1.

outlines the mechanical properties and glass transition temperatures of these materials. It is seen that in poly(TMO 650) based systems, the identity of the endgroups does not wield significant influence on final mechanical and thermal properties. Rather, the flexibility of the Poly(TMO) backbone exerts the major influence on the properties of the cured film regardless of the end group and produces a material which is rubbery at room temperature.

TABLE 2

Tensile Properties and Glass Transition Temperatures of Various Norbornene-Functionalized Poly(TMO 650) Resin

| N-Functionality (w PETMP) | Tensile Modulus (MPa) | Tensile Strength (MPa) | Elongation at Break (%) | Tg (°C.) |
|---|---|---|---|---|
| VI (Norbornene-methyl Carbonate Ester) | 4.70 ± 0.23 | 0.69 ± 0.05 | 17.3 ± 2.0 | −39.0 |
| VII (Norbornene Ester) | 5.62 ± 1.03 | 0.81 ± 0.11 | 16.7 | −39.0 |
| VIII (Norbornene Urethane) | 5.86 ± 0.28 | 1.17 ± 0.25 | 25.0 ± 6.6 | −16.0 |
| IX (Norbornene-amido Dimethylacetate) | 1.38 ± 0.28 | 0.53 ± 0.06 | 51.5 ± 7.7 | −20.0 |

The effect of polar functional groups on Tg in tile same oligomeric series is confirmed. Comparison of Tg values for IX (amide functional) and VIII (urethane functionality) with VI (carbonate ester) and VII (carboxylate ester) show stiffening due to restricted rotation of the amide and urethane groups and hydrogen bond formation. The Tg values for the former materials exceed the latter by approximately 2°–25° C., but still are well below published specifications for maximum desireable Tg for optical fiber primary coating materials.

TABLE 1

Properties of Norbornene Capped Tetramethylene Oxide/PETMP Formulations For Fiber Optic Coatings

| Property | Poly(TMO) 2900 Naz* (A) | Poly(TMO) 1000 Naz (B) | Poly(TMO) 2000 Naz (C) | Poly(TMO) 1000 Est** (D) | Poly(TMO) 2900 Est (E) | Blend (F) |
|---|---|---|---|---|---|---|
| $E_{30}$ | 428 | 483 | 388 | 248 | 438 | 358 |
| %$_{at\ break}$ | 58 | 32 | 44 | 25 | 76 | 38 |
| OIT*** | 221 | 190 | 157 | 201 | 238.3 | 212 |
| TGA$_{200°\ C.}$**** | OK | OK | OK | OK | OK | OK |
| Tg | −64.4 | — | — | −49 | — | −61.6 |
| H$_2$O Uptake | 0.3, −0.42 | 1.60, 2.0 | 1.7, 0.92 | 0,5, −0.2 | 0.63, −0.1 | −0.43 |

*Naz = Norbornenylazlactone terminated poly(TMO).
**Est = Norbornenecarboxylate (ester) Terminated poly(TMO).
***OIT is the oxidation induction temperature of a sample heated at 10° C. per minute under oxygen.
****TGA results are based on isothermal runs carried out at 200° C. for 40 minutes.

EXAMPLE 11

Endgroup Effects

The effect of various end groups on a single oligomeric backbone (poly[TMO 650]) was also investigated. Table 2

EXAMPLE 12

Procedure for preparation of proreacted poly(TMO) thiol monomer and formulation of thiol-ene compositions Poly(TMO) dinorbornene (17.93 g, 0.015 moles) and pentaerythritol tetra-(3-mercaptopropionate) (PETMP) (W. R. Grace; 12.20 g, 0.025 moles) were placed in a 250 ml round bottomed glass reaction flask equipped with an efficient mechanical stirrer and a liquid addition funnel. The mixture was stirred to provide a uniform emulsion of the two comonomers. A small aliquot was removed for IR spectral analysis. 2,2'-Azobis(2-methylbutanenitrile) (Vazo 67, DuPont; 0.041 g; 2.14×10$^{-4}$ moles) was added to the cloudy blend and the mixture was stirred and heated to an external oil-bath temperature of 85° C. over a period of 30 minutes. During this time the mixture clarified and became more viscous. Heating and stirring was continued for an additional 30 minutes. During this time another small aliquot was removed for IR analysis, which indicated complete consumption of the norbornene monomer. This new composition may be regarded as a mixture of higher functionalized thiol oligomers bearing poly(TMO)-norbornane backbones and tetra thiol PETMP.

The reaction mixture was cooled to ambient temperature and 1.68 g of a solution of a 20:1 premixture of DAROCUR 1173 and Q1301 was added to the stirred mixture along with an additional quantity of poly(TMO) dinorbornene (53.77 g, 0.045 moles). This part of the procedure was conducted under yellow lighting. The mixture was stirred for about 30 minutes and removed from the reaction flask. The product obtained is referred to as Formulation A and contains 20% excess norbornene monomer over the amount required for equivalent stoichiometry with thiol.

A stoichiometric equivalent composition was prepared by adding 0.30 g PETMP (0.6 m moles) to 10 g of Formulation A (3.0 m moles thiol; 7.2 mmoles dinorbornene). This product is referred to as Formulation B.

Both formulations were stored in the dark at ambient temperature for 24 hours. After this time both were, surprisingly, found to be clear and homogeneous. By comparison, a stoichiometric blend of PETMP and poly(TMO) dinorbornene, which had not been prereacted, was cloudy and had begun to separate into two phases. The new prereacted thiol terminated oligomers assist the miscibility of PETMP in poly(TMO) dinorbornene resins and permit the formulation of homogeneous single part products to be made from otherwise incompatible comonomer components.

The formulated products, A and B, were found to be highly sensitive to UV light. Both compositions fixtured glass slides in less than 1 second irradiation from a "Blak-Ray" lamp. A thin film of formulation A cured to give a tacky coating after 5 seconds UV exposure, whereas formulation B gave a tack-free film after a similar exposure.

The initial IR spectrum of the reaction product showed absorption peaks at 715 cm$^{-1}$ and at 2570 cm$^{-1}$ characteristic of the norbornene and thiol monomers, respectively.

The IR spectrum of the reaction product after heating gave absorbance values corresponding to a complete consumption of the norbornene monomer and 38% conversion of thiol. Since these values are close to those that would be expected from the complete reaction of the norbornene-(TMO) monomer with 2 equivalents of thiol (30% equivalents of norbornene in original mixture), the predominant molecular species of the prereacted polymer may be regarded as a hexafunctional thiol terminated poly(TMO)-dinorbornane having the structure:

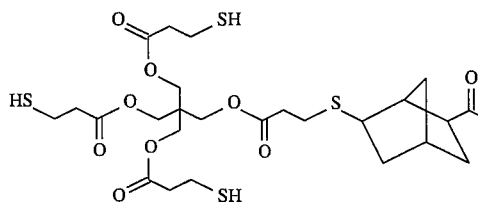
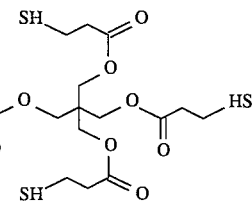

EXAMPLE 13

Photosensitivity and Degree of Cure of Poly(TMO) Dinorbornene-PETMP Resins Compositions The coating of optical fibers with UV curable compositions is performed in a continuous high speed process, frequently at speeds in the region of 10 m/sec. To be useful the primary coating composition must combine high photosensitivity in the uncured state and flexibility in the cured state. These characteristics tend to be mutually exclusive and are difficult to obtain. This experiment is designed to measure the photosensitive response of the poly(TMO) dinorbornene-thiol to UV light and to estimate the final extent of cure in the irradiated product. It is also an objective of the experiment to compare the performance of the new poly(TMO) resins with the prior art norbornene-thiol compositions.

A coating composition was prepared, under yellow lights, by blending together, in a mechanical mixer, the following materials:

| | |
|---|---|
| poly(TMO 1000) dinorbornene carboxylate (eq. wt. 639) | 12.783 g |
| PETMP (eq. wt. 122) | 2.459 g |
| 2-hydroxy-2-methyl-1-phenylpropan-1-one (DAROCUR 1173, photoinitiator, EM Industries) | 0.292 g |
| aluminum tris-N-nitrosophenylhydroxylamine (Q1301 thermal stabilizer, Wako) | 0.015 g |

The ratio of norbornene and thiol comonomers represent equivalent stoichiometry.

The blended product was obtained as a cloudy mixture owing to the incomplete miscibility of the norbornene and thiol components, as noted in the previous example. However, since bulk phase separation did not occur for several hours after mixing, it was possible to carry out the photochemical evaluation without the need to employ the prereacted resin.

To measure the photochemical response of the composition, a small sample was smeared onto a potassium bromide disc to give a uniform thin film of the product. The coated KBr plates were exposed to UV light from a high pressure short arc 500 W mercury lamp illuminator supplied by Oriel Corporation. Infrared radiation was removed by reflecting the beam from a 290–390 nm dichroic mirror. The UV light was focused through an optical integrator, collimating quartz lens and a narrow 365 nm bandpass filter (03 FIM 028, Meltes Griot) onto the coated KBr plate. This arrangement produces a 10 nm wide band of UV light, centered at 365 nm. The collimating lens ensures a uniform distribution of light intensity over the width of the salt plate. The dichroic mirror ensures that curing takes place at ambient temperature, even after long exposures. An electronically activated shutter, located directly after the optical integrator, was used to control the exposure time in 100 ms time intervals with a shutter open/close time of 20 ms.

The salt plates were placed directly below the bandpass filter in an anti reflective chamber to minimize possible errors due to reflected UV light. The incident radiant power (irradiance) was determined at the same position as the sample, prior to each experiment, using a calibrated radiometer (IL 1700) and detector (SED400), supplied by International Light Inc. The detector was equipped with a filter set, optimized for maximum sensitivity at 365 nm. Fluence (incident energy per unit area) was calculated from the product of irradiance and exposure time.

The norbornene/thiol polymerization reaction was followed by measuring absorbance changes in the infrared spectrum at 715 cm$^{-1}$. This peak, characteristic of the C—H asymmetric deformation of cis-alkenes is free of interference bands and is relatively intense compared to the S—H and C=C stretching vibrations. On prolonged UV exposure, the absorbance disappears completely. Absorbances were measured by standard base-line techniques and errors due to slight changes in film thickness were eliminated by measuring an absorbance ratio to an internal standard unaffected by UV exposure. Ratios were found to be constant over a range of film thickness, provided that the peak values were below about 1.0 absorbance units.

Assuming a linear relationship of absorbance with concentration, as defined by the Beer-Lambert law, the fractional conversion of ene monomer (F) is given by the equation:

$$F = 1 - Rt/Ro$$

where Ro and Rt are the absorbance ratios before and after UV exposure respectively.

The infrared analysis; was carried out directly following irradiation and performed on a Nicolet 205 FT IR spectrometer collecting 32 scans/spectrum at a resolution of 4 cm$^{-1}$. A separate sample film was prepared for each exposure time. The UV irradiance was 1.26 mW/cm$^2$.

The results obtained from this experiment are listed in Table 3.

TABLE 3

| Exposure Time (s) | Fluence (mJ/cm2) | Rt/Ro | F |
| --- | --- | --- | --- |
| 0 | 0 | 0.588 | 0 |
| 0.1 | 0.126 | 0.569 | 0.03 |
| 0.2 | 0.252 | 0.565 | 0.04 |
| 0.3 | 0.378 | 0.570 | 0.03 |
| 0.5 | 0.630 | 0.560 | 0.05 |
| 0.6 | 0.756 | 0.561 | 0.05 |
| 0.8 | 1.01 | 0.543 | 0.08 |
| 1.0 | 1.26 | 0.528 | 0.10 |
| 1.5 | 1.89 | 0.502 | 0.15 |

TABLE 3-continued

| Exposure Time (s) | Fluence (mJ/cm2) | Rt/Ro | F |
| --- | --- | --- | --- |
| 3.5 | 4.41 | 0.438 | 0.26 |
| 4.0 | 5 04 | 0-490 | 0.17 |
| 5.0 | 6.30 | 0.415 | 0.29 |
| 6.0 | 7.56 | 0.416 | 0.29 |
| 8.0 | 10.08 | 0.336 | 0.43 |
| 15 | 18.9 | 0.223 | 0.62 |
| 20 | 25.2 | 0.168 | 0.71 |
| 30 | 37.8 | 0.131 | 0.78 |

Figure 2:
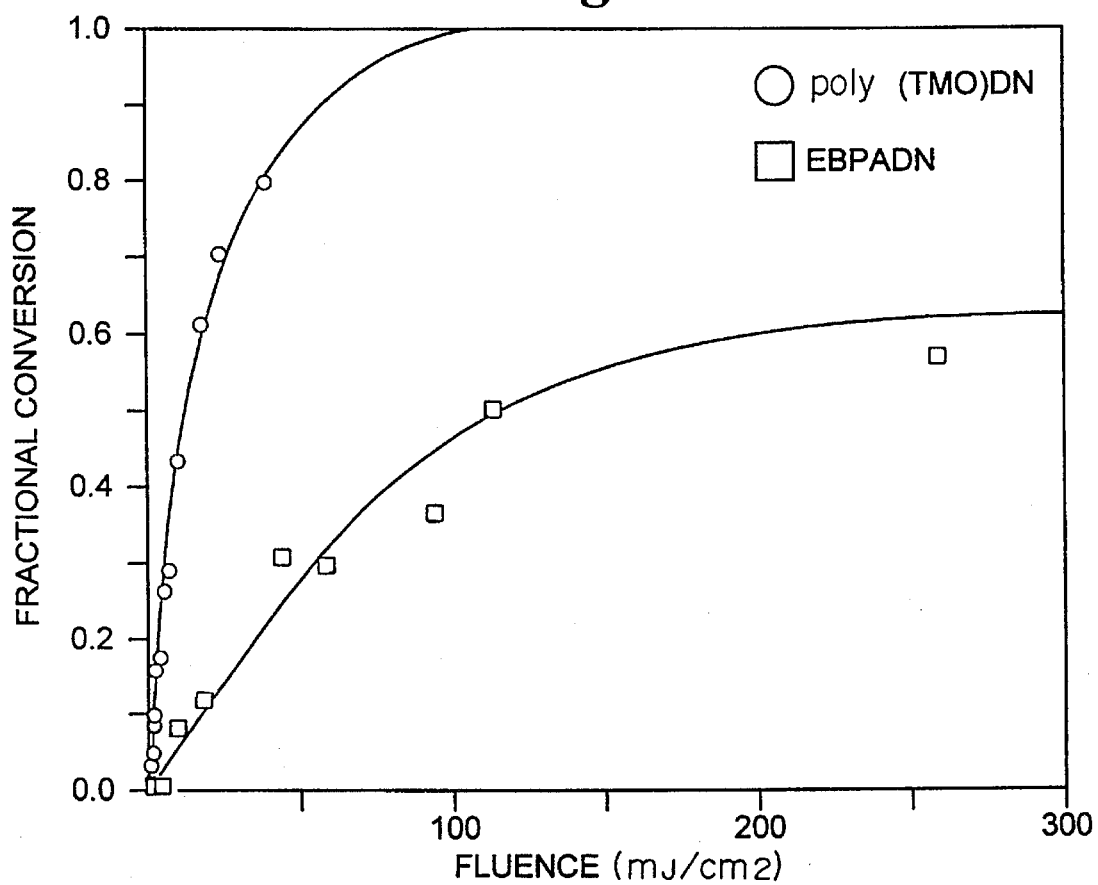
FIG. 2 is a plot of fractional conversion against fluence of UV irradiation comparing cure response of a formulation of the invention with a norbornene-thiol formulation based on a prior art norbornene resin.

As the UV dose delivered to the sample film is increased there is clearly an overall increase in the conversion of the norbornene monomer. By plotting the fractional conversion against the fluence, an overall evaluation of the cure response can be made. This plot, labeled as poly(TMO)DN, is shown in FIG. 2. A similar experiment was carried out using the dinorbornene carboxylate ester of ethoxylated bisphenol A (EBPADN), a prior art monomer, as a replacement for the poly(TMO) dinorbornene carboxylate material, in an equivalent stoichiometric composition with PETMP. The results of this experiment are also shown in FIG. 2, so that a comparison of the two systems may be made. In this second test the UV irradiance was 1.14 mW/cm$^2$ otherwise the experimental conditions were identical. It is unlikely that the small difference in light intensity would result in a significant difference in photocure response.

The data in FIG. 2 clearly shows the advantages of the new poly(TMO) dinorbornene monomers in comparison to the prior art materials. The photosensitivity of these products may be defined as the minimum energy required to immobilize the material.

Since alkene-thiol compositions cure by a step growth mechanism, the theoretical gel point may be predicted with some accuracy from a knowledge of the degree of functionality and the stoichiometric balance of the two comonomers. As described in C. Macosko and D. Miller, *Macromolecules*, 9, (2), 199 (1976), the fractional conversion at gel point, α, is given by the equation:

$$\alpha = \frac{1}{\sqrt{r(f_a - 1) \cdot (f_b - 1)}}$$

where $f_a$ and $f_b$ are the functionalities of the two comonomers and r is the stoichiometric imbalance defined as the ratio Na/Nb (Nb>Na), where Na and Nb are the number of reactive equivalents of each type of the two kinds of functional groups present. The values of Na and Nb may be estimated as the product of the functionality and number of moles of each comonomer present. If α is <1, then a crosslinked gelled polymer is predicted to be produced at that fractional conversion. If, on the other hand, α>1, then only non-crosslinked linear and/or branched polyfunctional oligomers are predicted to be produced. Such materials are polydisperse and polyfunctional in unreacted b groups. In the case where $f_1$ and $f_b$ are 2 and 4 for the diene and tetra thiol respectively and the formulation is stochiometrically balanced, i.e., r=1, the predicted gel point conversion occurs at a fractional conversion of 0.58. In relation to FIG. 2, where both compositions have been formulated such that r=1, it can be seen that the fluence required to gel the poly(TMO) composition is approximately 20 mJ/cm2, whereas the corresponding value required to gel the EBPADN product is approximately 300 mJ/cm2. Thus the photosensitivity of the present poly(TMO) products is 15 times greater than the prior art EBPADN containing compositions. This result is particularly surprising, since the molecular weight of the poly(TMO) monomer (1278) is twice the molecular weight of EBPADN (634).

In addition the new poly(TMO) resin containing composition has the added advantage of giving a higher extent of polymerization than is possible with the existing norbornene-thiol resins as exemplified by EBPADN. The poly(TMO) material gives up to 80% conversion with little reduction in reaction rate and may be projected to full cure with relatively little additional energy. The network structure is therefore essentially complete with little or no unreacted functional groups. This contributes to the mechanical performance of the cured composition, and renders the product less susceptible to further environmental, chemical and physical change. In contrast, the EBPADN has an ultimate conversion at or near the theoretical gel point of 58% and it can be seen from FIG. 2, that additional energy would not be expected to increase the conversion significantly. In this case the network is far from complete and a high concentration of unreacted norbornene and thiol groups are present in the cured structure. In this state the product is prone to further reaction after the initial curing stage, resulting in unpredictable changes in physical properties. This makes the material unsuitable for some applications, particularly for the primary coating of optical fibers.

The above equation may also be used to define the upper limits of the molar ratio of the norbornene and thiol monomers used in the production of the prereacted oligomer for compatabilizing the respective components of the compositions of the invention. Since the requirement is that the prereacted material be soluble in the unreacted norbornene, a gelled product must be avoided. The value of r must therefore be such that $\alpha$ is 1 or greater. In the examples of this application, a di-functional ene and tetra-functional thiol are employed and the corresponding values of $f_a$ and $f_b$ are therefore 2 and 4 respectively. By solving the equation for r, with $\alpha=1$, the maximum stoichiometric imbalance of these two comonomers that may be used to form the oligomer may be determined, viz. 0.33. Desireably, the oligomerization reaction should be run to complete conversion of the less abundant monomer, i.e. the norbornene material.

It should be noted that maximum allowable value of r will change according to the functionality of the comonomers. For example a tetra-functional ene and tetra-functional thiol will crosslink if the stoichiometric imbalance exceeds 0.11; a diene and trithiol will crosslink if the value exceeds 0.50, etc. If mixtures of different nene and thiol comonomers, having the same reactivity, are employed, then the functionalities $f_a$ and $f_b$ are replaced by the corresponding weight averaged values.

The lower limit on the value of r is determined only by the solubility difficulty encountered between the polythiol and norbornene components. There must be sufficient oligomer to enhance the solubility of the comonomers in the final formulation. Generally an oligomer formed from a norbornene/thiol mixture to improve solubility should have a value of r of at least $r^1/100$ (where $r^1$ is the value of r when $\alpha=1$) with a preferred value of at least $r^1/10$. The preferred range of comonomer concentrations for production of prereacted oligomers would therefore be between $r^1/10$ and $r^1$.

In Example 12 the oligomer has been prepared with the thiol in excess. It is expected that a prereacted oligomer prepared with excess alkene would provide the same benefits although the structure of the product would be different. The same definitions as to the stoichiometry apply regardless of which monomer is in excess.

Having prepared the oligomer, the final crosslinkable composition may be formulated by addition of the appropriate quantity of the depleted monomer along with photoinitiator and other additives. The overall stoichiometry will depend on the particular physical properties required of the crosslinked polymer. The value of r for the final composition must be selected such that $\alpha$ is less than 1. For the diene and tetra-thiol this translates to a value for r in excess of 0.33. Optimal properties are usually obtained when there is an exact equivalence of the two types of functional groups, i.e. r=1. However it is possible and sometimes desirable to modulate the properties by changing the stoichiometry.

Trithiol Based Formulations

The manufacturing of the coated optical fiber is dependent on several variables, one being the speed at which the manufacturer can draw the glass fiber, but another very important variable is the UV dose at which the primary coating is fully cured. The lower the UV dose required for full cure, the more the rate of manufacturing becomes almost entirely a function of the speed of drawing the optical fiber. By having a coating that requires a low UV dose for substantially complete cure, the manufacturer can concentrate on the glass processing. The UV dose required for substantially complete cure was measured by determination of the material's tensile modulus at several UV doses, since this also relates to the manufacturing need for the coating to quickly establish a solid structure. In Lee, et al, U.S. Pat. No. 5,169,879, the composition is defined as cured when the surface was tackfree and the physical properties near maximum (column 11, 64–66). This definition will be used in the work presented in the following examples.

UV Curing

Sample preparation was carried out under yellow lighting to eliminate all background UV radiation. A collimated Oriel UV light source (Oriel Corporation) was used for room temperature curing; this device uses a dichroic mirror to remove the infrared component of the light. Light intensity was measured with a radiometer (peak sensitivity 365 nm). Three measurements were taken before any samples were cured, and three after the last sample was cured. The average intensity was 22.80 mW/cm2. Shutter control within 0.1 second was possible using an Oriel electronic timer control. Although these conditions do not duplicate the curing conditions on a manufacturing line, they were chosen to show how rapidly the material achieves tack free dose and a tensile modulus that is at or near the maximum modulus, even at low ultraviolet intensities where no heat is provided to further promote the polymerization reaction. Many references, including U.S. Pat. No. 5,169,879; U.S. Pat. No. 5,139,872 and U.S. Pat. No. 4,956,198 refer to medium pressure Hg arc lamps, which are well known to those skilled in the art to emit UV radiation of much higher intensity and to emit a significant amount of heat during exposure. UV Fusion Systems, a manufacturer of a commonly used UV curing apparatus which incorporates medium pressure lamps, states in their "Operation and Maintenance Manual" that the surface temperatures of the lamp during normal operation will exceed 120° F. This in fact is exactly the system used in U.S. Pat. No. 4,956,198. In contrast, the use of low intensity UV radiation, and the ability to achieve full cure at low intensities, are advantages in terms of manufacturing set-up and maintenance costs (low intensity lamps are less expensive and it is less costly to retrofit an assembly line with lower-intensity lamps), in terms of minimizing possible worker hazards from exposure to stray high intensity UV beams, and also in prevention of heat exposure by and damage to sensitive components (electronic and otherwise).

Thin Film Sample Testing

An Instron 4505 Universal Testing Machine interfaced with Series IX software was used to measure tensile properties. This machine was equipped with a 10N (2.25 lb) dual tension/compression load cell and pneumatic clamps with rubber-faced grips. The load cell is accurate to 0.4%, or 0.041N (0.009 lb). The gage length used was 5.0 cm (1.97 in), and the crosshead speed was 2.5 cm/min (0.98 in/min). Tensile properties given in the examples are the average of 5–8 samples.

Glass transition temperature was obtained via dynamic mechanical analysis using a Rheometrics Dynamic Analyzer in the rectangular torsion mode. The range of strain at which the material's linear elastic region [LER] existed was first determined by several strain sweeps with the material at a temperature where it was in its glassy phase. Then, virgin material was used in a temperature sweep where the strain applied was within the material's LER, and the glass transition temperature (Tg) was taken as the temperature corresponding to the maximum in the tan δ peak. Values given for Tg are the average of two to three measurements, all made on virgin samples.

ASTM D-542 was used to obtain the refractive index, and a modified version of ASTM D-570 was used to obtain both water absorption and water extractibles. All numbers are the averages of three to four measurements.

Examples 14–17 sense the purpose of illustrating the glass transition temperature, refractive index, water absorption and speed of polymerization of formulations using trithiols. The trifunctional thiol used in these examples, trimethylolpropane trimercaptopropionate ([TMP]2), is immediately miscible in poly(tetramethylene oxide 1000) dinorbornene carboxylate [p(TMO 1000)DN], in a range of proportions, and a stoichiometric formulation has a viscosity between 500–800 cps [500–800 mPas]. The details of each formulation are given below.

EXAMPLE 14

1.0:1.0 Nene/thiol ratio formulation 36.25 g [TMP]2
162.7 g p(TMO 1000)DN
4.0 g DAROCUR 1173
0.2 g Q1301
0.1 gBHT
0.1 g MEHQ This formulation cured to tack-free films at a dose of 101.2 mJ/cm$^2$ with an average thickness of 9.3 mils (0.023 cm). At that dose, the tensile modulus was 313 psi [2.16 MPa], tensile strength was 134.6 psi [0.93 MPa] and elongation at break was 73.3%. At a dose of 303.8 mJ/cm$^2$, average film thickness was 9.4 mils (0.024 cm) and the tensile modulus was 316.1 psi [2.18 MPa], with a tensile strength of 111 psi [0.76 MPa] and an elongation to break of 53.0%. At a dose of ~987.2 mJ/cm$^2$, with average film thickness of 10.3 mils (0.026 cm) the modulus was 397 psi [2.74 MPa], tensile strength was 112 psi [0.76 MPa] and elongation at break was 43.4%. The glass transition temperature of this material was found to be −50.65° C. The index of refraction (nD) of the liquid was found to be 1.4841 at 25° C. Water absorption after 24 hours at room temperature was found to be 0.78% and extractibles were found to be 2.51%.

EXAMPLE 15

1.0:1.25 Nene/thiol ratio formulation 43.33 g [TMP]2
155.56 g p(TMO 1000)DN
4.0 g DAROCUR 1173
0.2 g Q1301
0.1 g BHT
0.1 g MEHQ When irradiated at a dose of 99.4 mJ/cm$^2$, tack-free films of average thickness 9.2 mils (0.023 cm) were produced with tensile modulus of 107.8 psi [0.74 MPa], tensile strength of 66.8 psi [0.46 MPa], and elongation at break of 125%. When the formulation was irradiated at 300.5 mJ/cm$^2$, films of average thickness 8.5 mils (0.022 cm), the tensile modulus was 128 psi [0.88 MPa], the tensile strength was 68 psi [0.47 MPa] and the elongation at break was 101%. At a dose of 987 mJ/cm$^2$, the films had an average thickness of 8.5 mils (0.022 era) with modulus of 143.1 psi [0.99 MPa], tensile strength of 81 psi [0.56 MPa] and elongation at break of 109%.

EXAMPLE 16

1.0:1.0 Nene/thiol ratio formulation with 4-acetoxystyrene 36.25 g [TMP]2
162.7 g p(TMO 1000)DN
4.0 g DAROCUR 1173
0.2 g Q1301
0.1 gBHT
0.1 g MEHQ
0.8 g 4-acetoxystyrene When this formulation was irradiated at a dose of 296.4 mJ/cm$^2$, tack-free films of average thickness 10.8 mils (0.027 cm) were produced with tensile modulus of 386 psi [2.66 MPa], tensile strength of 130 psi [0.90 MPa] and elongation at break of 55%. When irradiated at a dose of 987.2 mJ/cm$^2$, films had an average thickness of 10.6 mils (0.027 cm) with modulus of 407 psi [2.81 MPa], tensile strength of 161 psi [[1.11. MPa], and elongation at break of 68%. Water absorption after 24 hours at room temperature was found to be 0.56% and extractibles were found to be 3.15%.

EXAMPLE 17

1.0:1.25 Nene/thiol ratio Formulation with 4-acetoxystyrene 3.33 g [TMP]2
155.56 g p(TMO 1000)DN
4.0 g DAROCUR 1173
0.2 g Q1301
0.1 gBHT
0.1 g MEHQ
0.8 g 4-acetoxystyrene After irradiation of the formulation at a dose of 298 mJ/cm$^2$, tack-free films were produced having average thickness of 12.3 mils (0.031 cm) with tensile modulus of 118.3 psi [0.82 MPa], tensile strength of 66.5 psi [0.46 MPa] and elongation at break of 116%. After irradiation of the formulation at a dose of 992 mJ/cm$^2$, films of average thickness 11.0 mils (0.028 cm) had tensile modulus of 138 psi [0.95 MPa], tensile strength of 61 psi [0.42 MPa] and elongation at break of 77%

Thiol Prepolymer Formulations

Examples 18–21 serve the purpose of illustrating the glass transition temperature, refractive index, water absorption and speed of polymerization of formulations using a tetrathiol prepolymer. The tetrafunctional thiol used in these examples was prepared by combining 301.2 g p(TMO 1000)DN, 205.0 grams PETMP in a 950 ml widemouth amber glass bottle. The mixture was heated to 85° C. while stirred for 4 hours. After 4 hours, the extent of conversion was checked via IR and being acceptable, the bottle was capped and refrigerated.

All of the following samples were prepared by adding the necessary amount of norbornene (p(TMO 1000)DN) to a known amount of prepolymer in order to obtain either 1:1 stoichiometry (nene/thiol) or 1:1.25 nene/thiol stoichiometry. p(TMO 1000)DN was added to the prepolymer, and was mixed with an air motor until miscible (checked visually-no cloudiness, no interface between the two components). Then a premix containing photoinitiator, (DAROCUR 1173, 2 wt %), Q1301 and for examples 19 and 21, 2-propenylphenol (Aldrich) was added and further stirred. The onset of oxidation was measured using a Perkin Elmer TGA; tests were run in air at a scan rate of 5° C./min, with sample size between 2.2–3.2 mg. Formulations and properties obtained are shown below:

| Material | Example 18 | Example 19 | Example 20 | Example 21 |
| --- | --- | --- | --- | --- |
| Polythiol prepolymer | 138.6 g | 166.0 g | 138.6 g | 166.0 g |
| P(TMO 1000)DN | 191.4 g | 163.9 g | 191.4 g | 163.9 g |
| Q1301 | 1000 ppm | 1000 ppm | 250 ppm | 250 ppm |
| 2-propenyl phenol | 0 ppm | 0 ppm | 4000 ppm | 4000 ppm |
| Stoichiometry, nene:thiol | 1.0:1.0 | 1.0:1.25 | 1.0:1.0 | 1.0:1.25 |
| Properties | | | | |
| Tg, °C. | −50.3 | −50.3 | −50.3 | −50.6 |
| Refractive Index, Liquid | 1.4875 | 1.4894 | 1.4868 | 1.4892 |
| Water Absorption, % | 0.86 | 0.78 | 0.79 | 0.80 |
| Water Extractibles, % | 0.68 | 0.68 | 0.79 | 0.62 |
| Film cured at 100 mJ/cm$^2$: | | | | |
| Tensile Modulus, psi | 540 | 364 | 515 | 371 |
| [MPa] | [3.72] | [2.51] | [3.55] | [2.55] |
| Elongation at Break, % | 30.4 | 49.7 | 36.4 | 53.0 |
| Film cured at 300 mJ/cm$^2$: | | | | |
| Tensile Modulus, psi | 538 | 369 | 527 | 384 |
| [MPa] | [3.70] | [2.54] | [3.63] | [2.65] |
| Elongation at Break, % | 20.5 + | 35.4 + | 19.6 + | 32.0 + |
| | 3.3 | 7.4 | 4.5 | 8.4 |
| Onset of oxidation, °C. | 268.6 | 258.8 | 267.8 | 270.8 |

Since water absorption can adversely affect static fatigue and optical properties of optical fibers, a low degree of water absorption is considered very desirable for optical fiber coating materials. The water absorbtion of these formulations is excellent compared to prior art materials and the water extractables comparable to previously reported materials. See, for instance, U.S. Pat. No. 4,956,198; Chander P. Chawla and James M. Julian, "An Infrared Study of Water Absorption of UV Curable Optical Fiber Coatings", RadTech Report, January/February 1992, p.2428; and Jan Martin, "Contribution of Dual UV Cured Coatings to Optical Fiber Strength and Durability," (De Soto, Inc.), Radcure Europe '87, p.4–15.

EXAMPLE 22

A formulation was prepared as follows:

| Material | Amount, kg |
| --- | --- |
| pTMO(1000)DN | 12.11 |
| Treated [TMP]2 | 2.7 |
| LUCERIN TPO[1] | 0.111 |
| Acetoxystyrene | 0.06 |
| BHT | 0-0075 |
| MEHQ | 0.0075 |
| Q1301 | 0.0015 |

[1]Photoinitiator sold by BASF

PTMO(1000)DN was charged into reactor and stirred with nitrogen blanket. In a glass flask with nitrogen the treated (slurried with Magnesol and then filtered) [TMP]2 was mixed with Lucerin TPO until dissolved. Meanwhile, in a glass beaker with a magnet stirrer a premix of 4-acetoxystyrene, MEHQ, BHT and Q1301 were mixed until dissolved. This mixture was then added to the flask containing the thiol/Lucerin TPO solution and the resulting combination was stirred for 10 minutes. After that time the solution was added to the reactor, and all components of the formulation were mixed under nitrogen for 15 minutes. The formulation was then filtered through a 3-micron filter into a narrow-necked brown bottle.

EXAMPLE 23

A polythiol prepolymer was synthesized by combining 4.84 kg p(TMO 1000)DN and 3.3 kg PETMP which were mixed at 80° C. until full reaction had occurred. This was monitored via IR and required roughly 1½ working days for full reaction. The mixture was then cooled to 25° C. and flushed with nitrogen. Once the temperature had stabilized at 25° C., a stabilizer solution of 4-acetoxystyrene (0.079 kg), Q-1301 (0.002 kg), BHT (0.0119 kg) and MEHQ (0.0079 kg) was added. Additional (11.2 kg) unreacted pTHF(1000)DN was added to bring the stoichiometry to 1.0:1.0 nene/thiol. This combination was then mixed for 25 minutes. DAROCUR 1.173 was then added (0.572 kg) and mixing continued for 1 hour. The formulation was then filtered through a 25 micron bag into brown jugs.

EXAMPLE 24

Optical fiber which had been coated with either p(TMO 1000)DN/PETMP (Example 24) or p(TMO 1000)DN/[TMP]2 (Example 23) and a commercial secondary coating was tested. Properties studied included the temperature dependence of change in decibel per kilometer of fiber (dependence of attenuation on temperature), strip force, water absorption and water extractables, and pullout force.

Test methods used are well-known to those familiar with the art of manufacturing optical fibers. Properties are listed below.

| Property | Fiber Coated with Example 23 | Fiber Coated with Example 24 | Bellcore TR-20, issue 5 specification |
|---|---|---|---|
| Temperature dependence δdB/km (@ 1300/1550 nm) | | | |
| at −40° C. | 0.0/0.0 | 0.0/0.0 | <0.05 |
| at −60° C. | 0.0/0.0 | 0.0/0.0 | <0.05 |
| Strip Force (lb$_f$), dry | 0.75 | 0.78 | >0.3, <2.0 |
| Water Absorption, % | 0.62 | 0.64 | |
| Water Extractibles, % | 0.33 | 0.27 | |
| Pullout Force (lb$_f$) 50% RH | 1.31 | 1.23 | |

What is claimed is:

1. An optical fiber having a primary coating thereon of a crosslinked polymer which is the addition product, at 80% or greater conversion, of a polythiol and a polyene, the polyene being a compound having a plurality of norbornene groups thereon, one of the polythiol or the polyene having a backbone of a poly(tetramethylene oxide), the poly(tetramethylene oxide) having a number average molecular weight of between 250 and 5,000, the coating having been formed by curing a thiol-ene composition comprising said polythiol and said polyene or an oligomer of said polythiol and said polyene.

2. An optical fiber as in claim 1 wherein the composition further comprises a free radical photoinitiator.

3. An optical fiber as in claim 1 wherein said polyene is a norbornene terminated poly(tetramethylene oxide).

4. An optical fiber as in claim 3 wherein the ratio of norbornene groups in the polyene to thiol groups in the polythiol is between 1.0:0.8 and 1.0:1.3.

5. An optical fiber as in claim 3 wherein the norbornene terminated poly(tetramethylene oxide) is selected from the group consisting of:

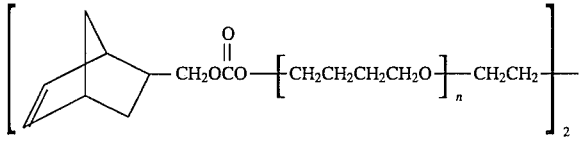

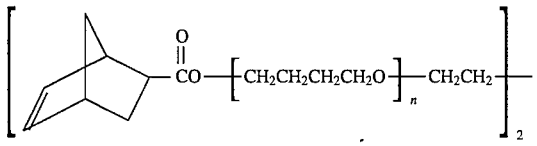

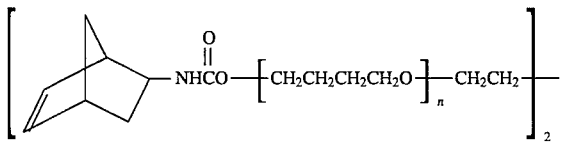

and

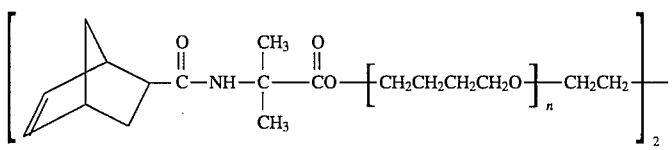

where n is an integer of 1–30.

6. An optical fiber as in claim 3 wherein the polythiol is fully miscible with the norbornene compound.

7. An optical fiber as in claim 1 wherein said thiol-ene composition comprises a thiol functional oligomer of polythiol and said polyene, said polyene being a norbornene terminated poly(tetramethylene oxide) having a number average molecular weight of between 250 and 5,000, and said polythiol having at least three thiol groups thereon.

8. An optical fiber as in claim 7 wherein the thiol functional oligomer is formed from a mixture of and polyene and said polythiol, the mixture having a value for r in the equation:

$$\alpha = \frac{1}{\sqrt{r(f_a - 1) \cdot (f_b - 1)}}$$

of between $r^1$ and $r^1/10$, where a is the fractional conversion at the gel point, $f_a$ and $f_b$ are the weight average functionalities of the polyene and polythiol components of said mixture, respectively, r is the stoichiometric imbalance defined as the ratio Na/Nb, where Na and Nb are, respectively, the number of equivalents of norbornene and thiol groups present in said mixture and $r^1$ is the value calculated for r when α=1.

9. An optical fiber as in claim 1 wherein the thiol-ene composition is a liquid having a viscosity of no more than 10,000 mPas at 60° C.

10. An optical fiber as in claim 9 wherein the thiol-ene composition is a liquid having a viscosity of no more than 2,000 mPas at 25° C.

11. An optical fiber as in claim 1 wherein the number average molecular weight of the poly(tetmmethylene oxide) is 650–1000.

12. An optical fiber as in claim 1 wherein the polythiol is selected from the group consisting of trimethylolethane tris-mercaptopropionate, trimethylolpropane tris-mercaptopropionate, trimethylolethane tris-mercaptoacetate, trimethylolpropane tris-mercaptoacetate, pentaerythritol tetramercaptoacetate, and pentaerythritol tetrakis-β-mercaptopropionate.

13. An optical fiber as is claim 3 wherein said crosslinked polymer has a Tg of −20° C. or less.

14. An optical fiber as is claim 13 wherein said crosslinked polymer has a Tg of −35° C. or less.

15. An optical fiber as is claim 13 wherein said crosslinked polymer has a Tg of −50° C. or less.

16. An optical fiber as is claim 14 wherein crosslinked polymer has a modulus of less than 800 psi (5.52 MPa).

17. An optical fiber as is claim 14 wherein said crosslinked polymer has a degree of water absorbtion of less than 1.0%.

18. A method of forming a primary coating on an optical fiber, the coating being a crosslinked polymer which is the addition product, at 80% or greater conversion, of a polythiol and a polyene, the method comprising applying a curable thiol-ene composition on the optical fiber, the curable thiol-ene composition comprising said polythiol and said polyene, or an oligomer of said polythiol and said polyene, said polyene king a Compound having a plurality of norbornene groups thereon, one of said polythiol or said polyene having a backbone of a poly(tetramethylene oxide), and the poly(tetramethylene oxide) having a number average molecular weight of between 250 and 5,000, and then subjecting the applied thiol-ene composition to U.V. irradiation having a fluence of less than 500 mJoules/cm$^2$.

19. A method as in claim 18 wherein said fluence is 300 mJoules/cm$^2$ or less.

20. A method as in claim 19 wherein said fluence is 100 mJoules/cm$^2$ or less.

* * * * *

UNITED STATES PATENT AND TRADEMARK OFFICE
CERTIFICATE OF CORRECTION

PATENT NO. : 5,558,937
DATED : September 24, 1996
INVENTOR(S) : Woods et al It is certified that error appears in the above-identified patent and that said Letters Patent is hereby corrected as shown below:

Col. 2, line 1, delete "Fiber" and insert -- fiber --;

Col. 2, line 42, delete "4,9:35,455" and insert -- 4,935,455 --;

Col. 3, line 33, delete "rates-" and insert -- rates. --;

Col. 9, line 41, delete "9°-100°C" and insert -- 90-100°C --;

Col. 12, line 40, delete "2°-25°" and insert -- 20-25° --;

Col. 20, line 55, delete "3.33" and insert -- 43.33 --;

Col. 21, line 31, delete "C./min" and insert -- C/min --;

Col. 21, line 59, delete all indications of "+" on the line

Col. 21, line 60, delete "3.3     7.4     4.5     8.4"

Signed and Sealed this

Seventeenth Day of December, 1996

Attest:

BRUCE LEHMAN

*Attesting Officer*        *Commissioner of Patents and Trademarks*